United States Patent [19]

Hagiwara

[11] Patent Number: 5,365,330
[45] Date of Patent: Nov. 15, 1994

[54] FOREIGN PARTICLE INSPECTION APPARATUS

[75] Inventor: Tsuneyuki Hagiwara, Kawasaki, Japan

[73] Assignee: Nikon Corporation, Tokyo, Japan

[21] Appl. No.: 979,276

[22] Filed: Nov. 20, 1992

[30] Foreign Application Priority Data

Nov. 27, 1991 [JP] Japan .................................. 3-335901
Nov. 27, 1991 [JP] Japan .................................. 3-335902

[51] Int. Cl.$^5$ ........................................... G01N 21/32
[52] U.S. Cl. ...................................... 356/237; 250/572
[58] Field of Search ............... 356/237, 239, 338, 339, 356/343, 445, 446, 73, 429–431, 394; 250/562, 563, 559, 571, 572

[56] References Cited

U.S. PATENT DOCUMENTS

| | | | |
|---|---|---|---|
| 4,669,875 | 6/1987 | Shiba et al. | 356/237 |
| 4,886,975 | 12/1989 | Murakami et al. | 356/237 |
| 4,889,998 | 12/1989 | Hayano et al. | 356/237 |
| 4,922,308 | 5/1990 | Noguchi et al. | 356/73 |

FOREIGN PATENT DOCUMENTS 0291347 10/1992 Japan .

Primary Examiner—Richard A. Rosenberger
Assistant Examiner—Hoa Q. Pham
Attorney, Agent, or Firm—Shapiro and Shapiro

[57] ABSTRACT

An apparatus for inspecting a foreign particle on an object to be inspected comprises a radiating device for radiating a light beam toward a surface to be inspected, which is at least one of a surface of a protection film supported by a frame member and a surface of a substrate provided with the protection film, a light receiving device for receiving light from the surface to be inspected to output a photoelectric signal, a detecting device for detecting the foreign particle based on the signal of the light receiving device, and an inspection area determining device for determining an inspection area on the surface to be inspected in accordance with an optical property of at least one of the frame member and the protection film.

26 Claims, 6 Drawing Sheets

FOREIGN PARTICLE INSPECTION APPARATUS

BACKGROUND OF THE INVENTION

1. Field of the Invention

The present invention relates to a foreign particle inspection apparatus. More particularly, the invention relates to an apparatus used in production of semiconductor devices, which is suitable for inspecting for foreign particle on at least one of a surface of a protection film (as will be referred to a pellicle film) supported by a frame member and a surface of a photo mask provided with a pellicle film.

2. Related Background Art

FIG. 9 is a perspective view to schematically show a construction of a conventional foreign particle inspection apparatus of such a type.

In FIG. 9, a reticle 101, which is a substrate to be inspected is fixed on a carrier arm 105, and a pellicle frame 102 is mounted on a pattern formed plane of the reticle 101. A pellicle film 103 is extended on the pellicle frame 102 to cover the pattern formed plane of the reticle 101. Inspection light emitted from a light source 107 is obliquely incident onto the reticle 101 via an oscillation mirror 108, which is scanning means. A certain range is scanned with the inspection light in the x-direction on the surface of the reticle 101 through oscillation of the mirror 108.

An inspection area on the reticle 101 is constant in the conventional inspection systems of such a type. The reticle 101 is moved by the carrier arm 105 in the y-direction simultaneously with the x-directional scan in order to scan the entire surface in the constant inspection area. Scattering-diffraction light generated by the pattern formed surface of the reticle 101 is received by a photodetector 104, which conducts a photoelectric conversion of the received light. A foreign particle is detected based on an output signal of the photodetector 104.

The inspection area in the conventional foreign particle inspection apparatus is next explained with reference to FIG. 10. FIG. 10 shows a condition in which the reticle 101 has been moved by the carrier arm (not shown) in the y-direction to move an inspection position from an inspection start position 106a on the reticle 101 (a point where the inspection light is first incident onto the reticle 101 without being interrupted by the pellicle frame 102) leftward to an inspection position 106b closer to an internal wall 102a on the left side of the pellicle frame 102. In FIG. 10, a solid line represents inspection light (incident light) incident from the light source (not shown) onto the reticle 101, and an alternate long and short dash line represents inspection light (receiving light) directing from the surface of the reticle 101 to the photodetector 104. Further, $I_1$ represents a direction of incident light at the inspection start position 106a, and $I_2$ a direction of incident light at the inspection position 106b.

As an incident angle $\alpha$ (an angle of incident light relative to a normal line to the reticle 101) and an light receiving angle $\beta$ (an angle of receiving light relative to a normal line to the reticle 101) increase, any pellicle film 103 generally decreases its transmittance. If the transmittance of the pellicle film 103 is not 100% for at least one of the incident angle $\alpha$ and the light receiving angle $\beta$, the incident light and the receiving light repeat reflection between the pellicle film 103 and the surface of the reticle 101.

Consider such a case that the internal wall 102a of the pellicle frame 102 is at an intersection 109a, 109b of optical paths of the incident light and the receiving light. The frame internal wall 102a is indirectly illuminated by the incident light $I_2$ to generate scattered light in such a case. The scattered light from the internal wall 102a exits on the optical path of the receiving light, so that it is received as stray light by the photodetector 104, which will be referred to as frame stray light.

The conventional foreign particle inspection apparatus is structured such that the incident angle $\alpha$ and the receiving angle $\beta$ are set small enough to reduce an amount of frame stray light, whereby the amount of stray light can be ignored in the inspection area A (FIG. 10) for any pellicle film.

There is, however, such a relation between either the incident angle $\alpha$ or the receiving angle $\beta$ as described and the foreign particle inspection capability that an intensity of scattered light from a foreign particle increases as the incident angle $\alpha$ or the receiving angle $\beta$ becomes larger, thereby to enhance the foreign particle inspection capability. In the conventional foreign particle inspection apparatus, if an inspection object is a pellicle film or a photo mask with a pellicle film, a location arrangement for radiating means and light receiving means of inspection light would be extremely restricted, whereby the inspection precision cannot be improved. Also, since the inspection area is always constant in the conventional system, there is such a problem that an area close to the frame internal wall cannot be inspected even in case of using a pellicle film and/or a pellicle frame which are relatively unlikely to cause scattered light.

SUMMARY OF THE INVENTION

The present invention has been accomplished taking into account the above circumstances. It is an object of the present invention to provide an apparatus capable of conducting a high precision foreign particle inspection without influence from frame stray light in inspection on at least one of a pellicle film surface and a photo mask surface on which a pellicle film is mounted, in which an optimum inspection area can be efficiently set in accordance with a sort (type) of pellicle film and/or pellicle frame.

It is another object of the present invention to provide an apparatus capable of conducting a high precision foreign particle inspection without influence from frame stray light, in which an optimum inspection area can be efficiently set independently for each of plural light receiving means in accordance with a sort (type) of pellicle film and/or pellicle frame.

In one aspect of the present invention, a foreign particle inspection apparatus comprises radiating means for radiating a light beam toward a surface to be inspected which is at least one of a surface of a protection film (pellicle film) supported by a frame member and a surface of a photo mask provided with the protection film, light receiving means for receiving the light from the surface to be inspected to conduct a photoelectric conversion thereof, and detecting means for detecting a foreign particle on the surface to be inspected based on a detection signal of the light receiving means, in which inspection area setting means is further provided for determining setting an inspection area on the surface to be inspected in accordance with an optical property of at least one of the frame member and the protection film.

In another aspect of the present invention, a foreign particle inspection apparatus comprises radiating means for radiating a light beam toward a surface to be inspected which is at least one of a surface of a protection film supported by a frame member and a surface of a photo mask provided with the protection film, a plurality of light receiving means for receiving light from the surface to be inspected to conduct a photoelectric conversion thereof, and detecting means for detecting a foreign particle on the surface to be inspected based on detection signals of the light receiving means, in which inspection area setting means is further provided for determining an inspection area on the surface to be inspected independently for each of the plural light receiving means in accordance with an optical property of at least one of the frame member and the protection film.

A specific arrangement of the inspection area setting means is as follows in the present invention. For example, in an embodiment in which an inspection area is set for each of the plural light receiving means, the apparatus has measuring means for each of the plural light receiving means for measuring an amount corresponding to a light amount of scattered light from the frame member received by the light receiving means when the light beam is radiated toward the surface to be inspected, and the inspection area setting means sets the inspection area based on measurement results of the measuring means.

Further, the inspection area setting means may have memory means for storing information measured by the measuring means for each kind of at least one of the frame member and the protection film, and the inspection area setting means may set the inspection area based on the information stored in the memory means.

An operation of the present invention will be explained with reference to FIGS. 8A to 8C. In FIG. 8A, a pellicle film 3 is held by a pellicle frame 2 which is mounted on a pattern formed plane of a reticle 1. An inspection point 6 on the reticle 1 is obliquely irradiated with inspection light I, and the inspection light I is reflected by a surface of the reticle i to enter a photodetector 4. In the drawing, a solid line represents inspection light (incident light) incident from a light source (not shown) onto the reticle 1, and a dashed line represents light (receiving light) directing from the surface of the reticle 1 to the photodetector 4. Only a principal ray is shown for each of the incident light and the receiving light for brevity.

When the reticle 1 is moved in the y-direction in FIG. 8A to move the inspection point on the reticle 1, an internal wall 2a of the pellicle frame 2 relatively approaches the inspection point. This state is shown in FIG. 8B, in which the inspection point is moved to a point 6'. In FIG. 8B, the inspection light I' repeats reflection between the pellicle film 3 and the surface of the reticle 1 to illuminate a point i on the frame internal wall 2a. A point d on the internal wall is disposed on an optical path corresponding (through repeated reflections between the pellicle film 3 and the surface of the reticle 1) to an acceptance optical axis at an angle $\gamma$ between the photodetector 4 and the reticle 1. If a light emitting point is on this optical path, its light enters the photodetector 4.

There are four intersections $y_a$, $y_b$, $y_c$, $y_d$ between the optical path of the incident light advancing with plural reflections and the optical path corresponding to the acceptance optical axis. While the reticle 1 is further moved in the y-direction as shown, the frame internal wall 2a passes through each of the intersecting positions in order from the intersection $y_d$ to the intersection $y_a$. When the frame internal wall 2a is present at each of the intersecting positions, the frame internal wall 2a is illuminated by the incident light to cause scattered light. Since the scattered light is on the optical path corresponding to of the acceptance optical axis, the light enters the photodetector 4.

FIG. 8C is a drawing corresponding to FIG. 8B taking into consideration solid angles of the respective optical fluxes of the radiation optical system and the light receiving optical system. FIG. 8C shows optical paths of outermost light rays for each of the incident light and the receiving light. Thus, when the frame internal wall 2a is present in areas as shown by $y_a'$, $y_b'$, $y_c'$, $y_d'$, the internal wall 2a is illuminated by the inspection light, and, therefore, the scattered light from the internal wall 2a enters the photodetector 4.

An incident light amount of frame stray light increases in that state, (1) as a surface of the internal wall 2a becomes rougher;

(2) as a reflectivity of the pellicle film 3 becomes larger at the incident angle (angle $\alpha$ in FIG. 10);

(3) as a reflectivity of the pellicle film 3 becomes larger at the light receiving angle (angle $\beta$ in FIG. 10);

(4) as the number of reflections of the incident light becomes less;

(5) as the number of reflections of the receiving light becomes less; and (6) as the angle of the optical axis of the light receiving system relative to the incident plane becomes smaller.

Therefore, the incident light amount of scattered light increases as the frame internal wall 2a moves from $y_d$ to $y_a$ in FIG. 8B, increasing influence on an inspection operation.

The present invention has been attained with recognition that the scattered light amount from the frame internal wall depends upon the above (1) to (3), that is, on a condition of at least one of the pellicle film and the pellicle frame. In one aspect of the present invention, the inspection area is changeably set in accordance with an optical property of the pellicle film and/or the pellicle frame, which was constant in the conventional system regardless of a kind of the pellicle film or the pellicle frame.

Specifically, in the present invention, it is preliminarily measured for each kind of pellicle film or pellicle frame whether stray light with an amount sufficient to cause a trouble in inspection enters the photodetector as the frame internal wall approaches the inspection point, and an optimum inspection area is set based on the information in accordance with a kind of the pellicle film or the pellicle frame, which is an inspection area without influence of the frame stray light but with the greatest coverage of a necessary inspection range.

In this case, if the pellicle film or the pellicle frame is likely to cause the frame stray light (i.e., if the pellicle film has a low transmittance to the inspection light or if the surface of the frame internal wall is rough), it is considered that an inspection possible area would be narrower than the necessary inspection range. It is possible to deal with the situation by changing an orientation of the reticle to be inspected, (for example, by relocating an area remaining uninspected in the y-direction), or, by decreasing the incident angle α and the receiving angle β as described for a portion close to the frame internal wall.

Further, if the pellicle film and the pellicle frame are unlikely to cause the frame stray light, that is, for example if the pellicle frame is treated by the low reflection treatment (which is smoothing of the internal wall or provision of the irregular reflection preventing member as detailed in Japanese Patent Application No. 3-56935, laid-open under Laid-Open No. 4-291347), it is possible to set an arbitrary inspection area to cover the entire necessary inspection range.

In another aspect of the present invention, an inspection area is set for each of plural light receiving means in accordance with an optical property of the pellicle film or the pellicle frame, which was constant in the conventional system regardless of a kind of the pellicle film or the pellicle frame.

Specifically, it is preliminarily measured for each kind of the pellicle film or the pellicle frame whether an amount of stray light sufficient to cause a trouble in inspection enters the photodetector as the frame internal wall approaches the inspection point. An optimum inspection area (maximum area to cover the necessary inspection range without influence from the frame stray light) may be set for each of the light receiving means in accordance with a kind of the pellicle film or the pellicle frame based on the information.

In this case, if the pellicle film and the pellicle frame are unlikely to cause the frame stray light, an arbitrary inspection area may be set to cover the entire necessary inspection range.

If the pellicle film and the pellicle frame are likely to cause the frame stray light (i.e., if the pellicle film has a low transmittance to the inspection light or if the frame has a high reflectivity), it is conceivable that an inspection possible region for one of the light receiving means would become narrower than the necessary inspection range. However, since the foreign particle inspection apparatus of the present invention has the plural light receiving means and an inspection area is set for each of the light receiving means, any necessary inspection range may be always covered by combining inspection possible regions for the respective light receiving means.

If it is taken into consideration that scattering properties of an actual foreign particle are unknown, it is important to conduct the foreign particle inspection using a plurality of light receiving means directed toward a surface to be inspected along different directions. According to the present invention, an inspection area which can cover as wide a necessary inspection range as possible without influence from the frame stray light may be set for each of the light receiving means, so that an overlap portion among the respective inspection areas may be maximized so as to improve the inspection precision.

DESCRIPTION OF THE PREFERRED EMBODIMENTS

Figure 1:
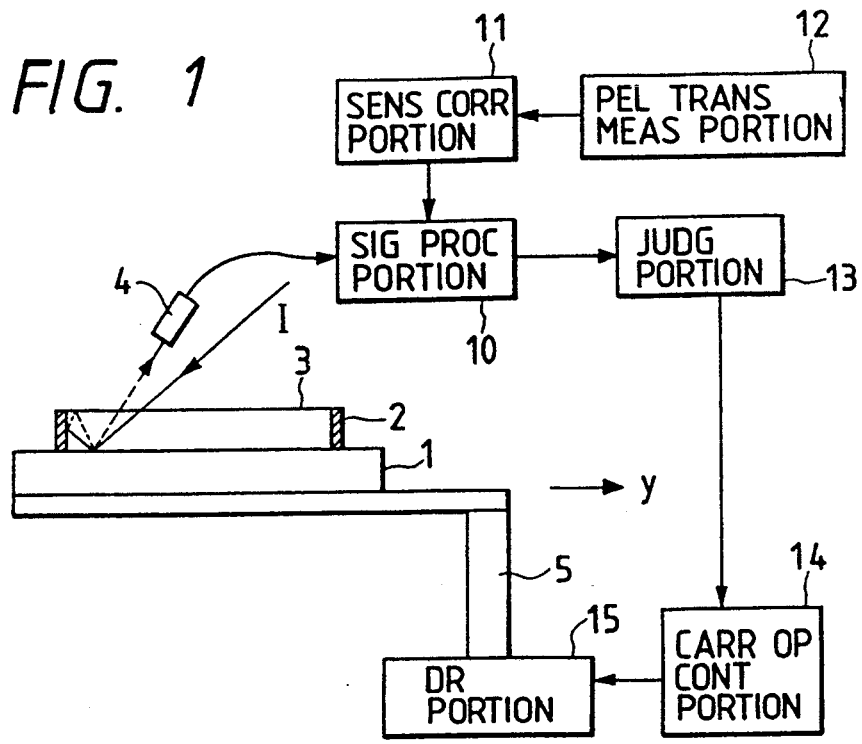
FIG. 1 is a schematic constitutional drawing to show a first embodiment of a foreign particle inspection apparatus according to the present invention.

Embodiments of the present invention are explained in the following with reference to the accompanying drawings. First, FIG. 1 is a constitutional drawing of a foreign particle inspection apparatus according to the first embodiment of the present invention. In FIG. 1, a pellicle frame 2 is mounted on a reticle 1 to surround a pattern formed area, and a pellicle film 3 is extended on the pellicle frame 2.

Inspection light (incident light) emitted from a light source (not shown) is obliquely incident via an oscillation mirror (not shown) as scanning means onto the reticle 1. It is preferable that an incident angle of the inspection light I is set between 80° and 10° for the inspection light I not to be interrupted by the pellicle frame 2. The inspection light I scans through the oscillation mirror in a predetermined range in the x-direction (direction normal to the sheet plane) on the reticle 1. In the scanning, there is normally no problem of frame stray light caused by the frame internal wall along the y-direction, so that a scanning range in the x-direction is preliminarily determined at a certain range.

The reticle 1 with the above pellicle film 3 is fixed on a carrier arm 5. The carrier arm 5 is constructed as movable in the y-direction by a drive portion 15, preferably as rotatable on the xy plane. An amount of y-directional movement of the carrier arm 5 may be measured by a length measuring machine such as a linear encoder, and is controlled at a certain value by a carrier control portion 14 based on a signal from a judging portion 13 as described later.

The x-directional scanning through the oscillation mirror and the y-directional movement of the carrier arm 5 allow the inspection light to evenly scan the entire surface in an inspection area (as described later) preliminarily set. Light generated from the reticle 1 to be inspected is received by a photodetector 4, in which the light is subject to a photoelectric conversion. The photoelectrically converted signal from the photodetector 4 is transferred to a signal processing portion 10 to detect a foreign particle based on the signal. There is no specific restriction on signal processing to detect a foreign particle, but, for example, a foreign particle may be discriminated from a regular pattern by using a fact that scattering-diffraction light from the pattern is relatively highly directional, but that from a foreign particle is relatively non-directional.

Further, in case that a surface inspection is carried out through the pellicle film 3 as shown in FIG. 1, it is desirable to effect a sensitivity correction on the photodetector 4 in accordance with a transmittance of the pellicle film 3. In the present embodiment, the inspection apparatus is so structured as to control the signal processing portion 10 by a command from a pellicle transmittance measuring portion 12 and a sensitivity correction portion 11 to conduct the entire inspection automatically. The transmittance of the pellicle may be preferably measured with light of the same wavelength as the inspection light I being radiated toward the pellicle film 3 at an incident angle and at a receiving angle for actual inspection.

Next explained are a structure and an operation for setting the inspection area in the present embodiment.

The present embodiment is structured such that scattered light from the pellicle frame 2 is measured using a light receiving system for insecting foreign particle (photodetector 4 in FIG. 1) in order to set an inspection possible area with a threshold value being always constant in a light receiving sensitivity condition equivalent to that upon actual foreign particle inspection. The light receiving sensitivity is corrected by a loss according to the transmittance of the pellicle through a command from the transmittance measuring portion 12 and the sensitivity correction portion 11 as described. A stroke of the carrier arm 5 is fully extended in the y-direction in the present embodiment as compared to the conventional apparatuses. This is because the inspection point should be made closer to the frame in case of foreign particle inspection of the reticle using a frame treated by the low reflection treatment or in case of measurement of the inspection possible area.

Now, in measuring the inspection possible area, the reticle 1 is first moved by the drive portion 15 and the carrier arm 5 up to a measuring position where the scattered light from the pellicle frame 2 may be received, in a desired inspection area. FIG. 1 shows this state. Then, the surface of the reticle 1 is scanned in the y-direction with the incident light I through the oscillation mirror (not shown), while the frame internal wall 2a is scanned with reflection light from the reticle 1. Scattered light from the frame internal wall 2a is received by the photodetector 4, in which the received light is subject to the photoelectric conversion. A signal photoelectrically converted in the photodetector 4 is supplied through the signal processing portion 10 to the Judging portion 13.

There is a threshold value preliminarily set for frame stray light amount in the judging portion 13. (The threshold value is set considering whether the frame stray light amount causes a trouble in actual foreign particle inspection.) It is judged in the judging portion 13 whether the signal from the photodetector 4 exceeds this threshold value. If the signal is below the threshold value, the judging portion 13 sends a signal to the carrier motion control portion 14 to move the carrier arm 5 by the drive portion 15 in the y-direction so as to make the inspection point further approach the frame internal wall 2a. It is judged in the judging portion 13 whether a frame stray light amount at that position exceeds the threshold value or not. Repeating the above operation, a position of the inspection point where the frame stray light amount exceeds the threshold value (a limit position in the y-direction) may be measured, whereby the inspection possible area may be determined.

Alternatively, the inspection area may be determined as follows. The frame internal wall 2a is scanned with reflection light from the reticle 1 at the measuring position (the condition of FIG. 1) where the scattered light from the pellicle frame 2 may be received, and a sort (type) of the frame 2 is judged with the signal from the photodetector in the scanning, whereby a proper inspection area may be selected from some inspection areas preliminarily set.

If the frame stray light amount does not exceed the threshold value while the inspection point approaches the frame internal wall 2a, that is, if the judging portion 13 judges that an appropriate low reflection treatment is provided on the frame 2 (or if the transmittance is approximately 100% for the inspection light of the pellicle film 3), an arbitrary inspection area may be set within a range in which the inspection light I is not interrupted by the frame 2.

In actual foreign particle inspection, information about the inspection possible area is supplied from the judging portion 13 to the carrier motion control portion 14, and the carrier motion control portion 14 controls the drive portion 15 based on this information. Then, the entire surface within the thus-set inspection area is scanned with the inspection light I through the x-directional scanning through the oscillation mirror and the y-directional movement of the carrier arm as described to conduct the foreign particle inspection. An inspection result is displayed on display means not shown.

If the set inspection area is insufficient for the necessary inspection range, an orientation of the reticle 1 is changed (turned by the carrier means 5 on the xy plane) to carry out inspection of an area remaining uninspected.

Figure 2:
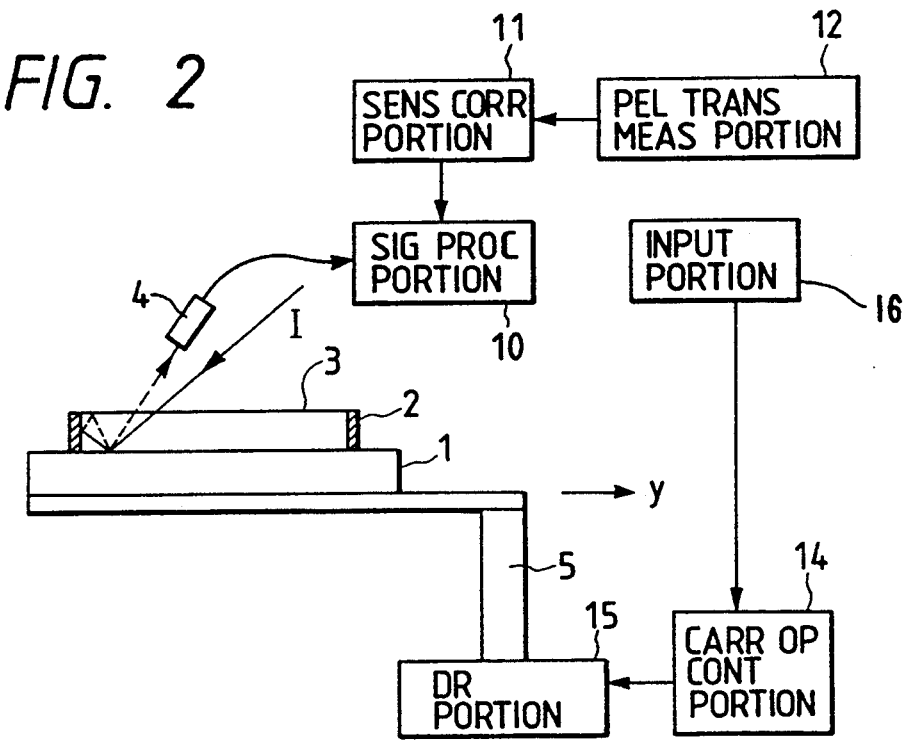
FIG. 2 is a schematic constitutional drawing to show a second embodiment of the foreign particle inspection apparatus according to the present invention.

FIG. 2 shows the second embodiment of the present invention. The second embodiment is different from the first embodiment in a structure to determine the inspection possible area. The other arrangement is same as that in the first embodiment. Specifically, in the second embodiment as shown in FIG. 2, an input portion 16 comprising for example a key board, a bar code reader, or the like is provided in place of the judging portion 13 as shown in FIG. 1, through which respective kinds of the pellicle film 3 and the pellicle frame 2 may be input from the outside.

In the second embodiment, an inspection possible area is preliminarily measured (similarly as in the first embodiment) for each kind of the pellicle film 3 or the pellicle frame 2 mounted on the reticle 1 to be inspected, and measurement results are stored in the apparatus for each kind of the pellicle film 3 or the pellicle frame 2. An optimum inspection area may be set in actual inspection by comparing kinds of the pellicle film 3 and the pellicle frame 2 input into the input portion 16 with data about the above inspection possible area preliminarily stored.

The present embodiment may be further arranged such that the sensitivity correction value of the photodetector 4 may also be input from the outside in accordance with the transmittance of the pellicle film 3, in addition to the data about the inspection possible area. Although the above first and second embodiments are explained about the example to inspect the reticle surface with the pellicle film mounted thereon, it is needless to say that the foreign particle inspection apparatus of the present invention may be applicable to foreign particle inspection of the pellicle film itself.

Further, according to the present invention, since there is no extreme restriction on the location of the radiating means and the light receiving means of the inspection light, a preferable location arrangement of the radiating means and the light receiving means of the inspection light can be determined to improve the inspection capability for a foreign particle whereby the inspection precision may be improved.

Figure 3:
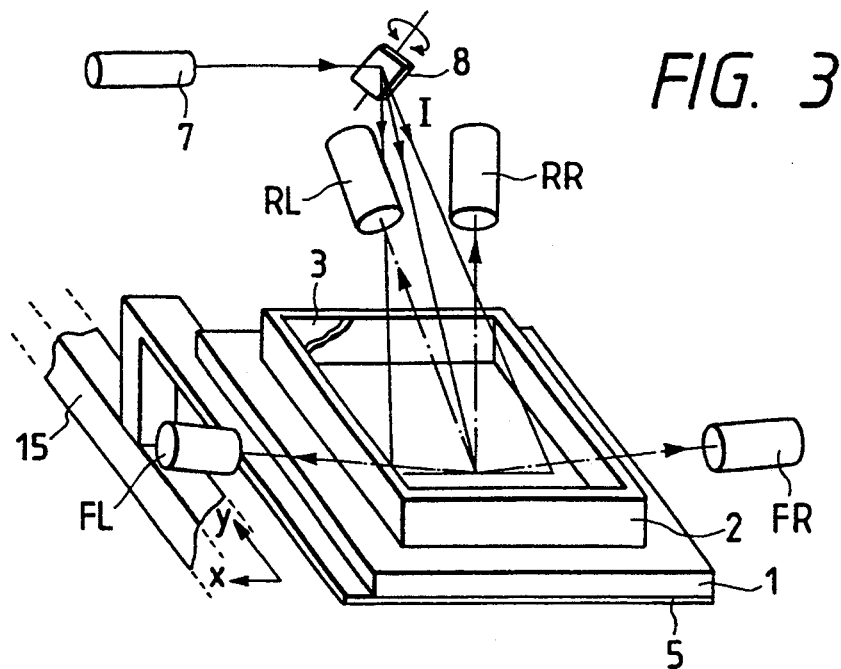
FIG. 3 is a perspective view to show a construction of an optical system in a third embodiment of the foreign particle inspection apparatus according to the present invention.
Figure 4:
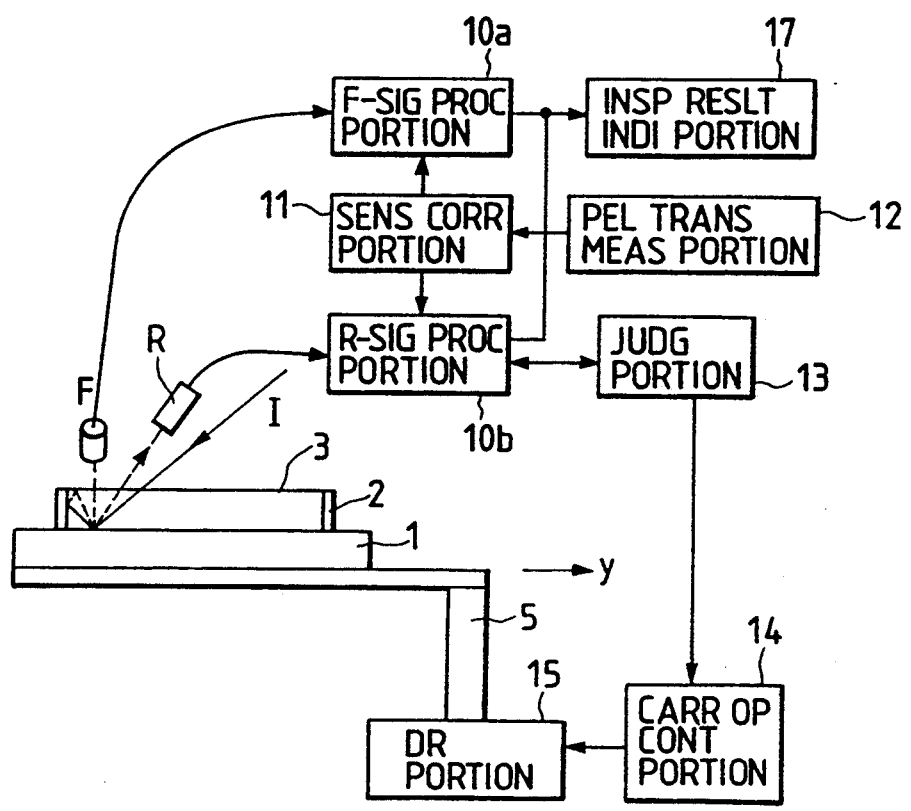
FIG. 4 is a constitutional drawing to show a total construction of the foreign particle inspection apparatus in the third embodiment of the present invention.

FIG. 3 is a perspective view to show a construction of an optical system in a foreign particle inspection apparatus according to the third embodiment of the present invention. FIG. 4 is a schematic constitutional drawing to show the entire foreign particle inspection apparatus according to the third embodiment. The same members are given the same numerals as in the aforementioned embodiments. In the drawings, a pellicle frame 2 is mounted on a reticle 1 to surround a pattern formed area, and a pellicle film 3 is extended on the pellicle frame 2.

Inspection light (incident light) emitted from a light source 7 is obliquely incident via an oscillation mirror 8 as scanning means onto the reticle 1. An incident angle of the inspection light I preferably set between 80° and 10° in order that the inspection light I is not interrupted by the pellicle frame 2. The reticle 1 is scanned with the inspection light I through the oscillation mirror in a certain range in the x-direction. Since frame stray light normally causes no problem on the frame internal wall along the y-direction, a certain range is preliminarily determined for x-directional scanning range.

The reticle 1 with the above pellicle film 3 is fixed on a carrier arm 5, and the carrier arm 5 is structured movable in the y-direction and rotatable in the xy plane by a drive portion 15. An amount of movement of the carrier arm 5 is measured by a length measuring machine such as a linear encoder, and is controlled to a certain value by a carrier control portion 14 based on a signal from a judging portion 13 as described later.

The x-directional scan through the oscillation mirror and the y-directional movement of the carrier arm 5 allow the inspection light to evenly scan the entire surface in the inspection area (as described later) preliminarily set. Light from the reticle to be inspected 1 is received by photodetectors FL, FR, RR, RL, which respectively carry out a photoelectric conversion. In the present embodiment, the photodetectors RR, RL have respective optical axes along a direction substantially parallel to an incident plane of the inspection light, and face the reticle 1 in the incident direction of the inspection light I. The photodetectors FL, FR have respective optical axes along a direction substantially perpendicular to the incident plane of the inspection light, and face the reticle 1 in the scanning direction (x-direction) with the inspection light I. A photodetector R as shown in FIG. 4 represents the photodetectors RL, RR as shown in FIG. 3, and a photodetector F as shown in FIG. 4 does the photodetectors FL, FR as shown in FIG. 3.

Photoelectrically converted signals from these photodetectors F and R are sent to respective signal processing portions 10a and 10b, to conduct foreign particle detection based on the signals. Although there is no specific restriction on the signal processing for foreign particle detection, a foreign particle may be discriminated from a regular pattern for example by using a fact that scattering-diffraction light from the pattern is relatively highly directional, but scattering-diffraction light from a foreign particle is relatively non-directional.

In case that surface inspection is carried out through the pellicle film 3 as in the present embodiment, it is desirable to effect sensitivity correction on the photodetectors F and R in accordance with a transmittance of the pellicle film 3 in order to compensate a decrease in photoelectrically converted signals due to intervention of the pellicle film 3. The present embodiment is structured such that the signal processing portions 10a, 10b may be controlled by a command from a pellicle transmittance measuring portion 12 and a sensitivity correction portion 11 to automatically conduct the entire inspection. The transmittance of the pellicle film 3 is preferably measured with light of the same wavelength as the inspection light I being radiated toward the pellicle film 3 at the incident angle and at the receiving angle for actual inspection.

Next explained are a structure and an operation for setting an inspection area in the present embodiment.

The present embodiment is structured such that an inspection possible area of the photodetector R is measured using the photodetector R having the optical axis along the direction substantially parallel to the incident plane of the inspection light I in order to set the inspection possible area with a threshold value being always constant in a light receiving sensitivity condition equivalent to that in actual foreign particle inspection, A light receiving sensitivity is to be corrected by a loss in accordance with the transmittance of the pellicle film through the command from the transmittance measuring portion 12 and the sensitivity correction portion 11 as described. A y-directional stroke of the carrier arm 5 is fully extended as compared to that in the conventional apparatuses. This is because the inspection point should be made closer to the frame in measuring the inspection possible area or in conducting the foreign particle inspection of the reticle using the frame treated by the low reflection treatment.

Now, in measuring an inspection possible area of the photodetector R, the reticle 1 is first moved by the drive portion 15 and the carrier arm 5 up to a measuring portion where scattered light from the pellicle frame 2 may be received in a desired inspection area. FIG. 4 shows this state. Then, the incident light I scans the surface of the reticle 1 through the oscillation mirror 8 in the x-direction, while reflection light from the reticle 1 scans the frame internal wall 2a. The scattered light from the frame internal wall 2a is received by the photodetector R to be subject to the photoelectric conversion, and a photoelectrically converted signal from the photodetector R is supplied through the signal processing portion 10 to the judging portion 13.

In the judging portion 130 a threshold value is preliminarily set for frame stray light amount. (The threshold value is set considering whether the frame stray light causes a trouble in actual foreign particle inspection.) It is judged in the judging portion 13 whether the signal from the photodetector R exceeds this threshold value. If the frame stray light amount is below the threshold value, the Judging portion 13 sends a signal to the carrier motion control portion 14 to move the carrier arm 5 by the drive portion 15 in the y-direction so as to make the inspection point further approach the frame internal wall. Then, it is judged in the judging portion 13 whether a frame stray light amount at that point exceeds the threshold value or not. Repeating the above operation, a position of the inspection point where the frame stray light amount exceeds the threshold value (a limit position in the y-direction) may be measured, whereby an inspection possible area may be determined.

Alternatively, the inspection possible region may be determined as follows. A kind (type) of the frame 2 is judged by the signal from the photodetector R in scanning of the frame internal wall 2a with the reflection light from the reticle 1 at the measuring position (the condition of FIG. 4) where the scattered light from the pellicle frame 2 may be received, and a suitable inspection area may be selected from some inspection areas preliminarily set.

If the frame stray light amount does not exceed the threshold value upon approach of the inspection point to the frame internal wall 2a, that is, if the judging portion 13 judges that the frame 2 is treated by a proper low reflection treatment (or if the transmittance of the pellicle film 3 is approximately 100% to the inspection light) an arbitrary inspection area may be set within a range where the inspection light I is not interrupted by the frame 2.

Figure 6:
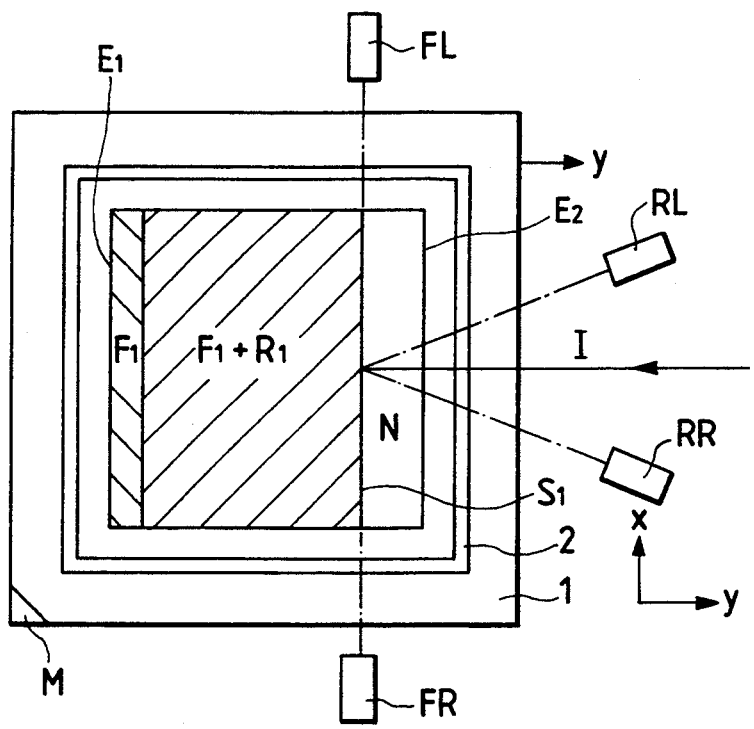
FIG. 6 is a conceptual drawing to illustrate the foreign particle inspection operation in the third embodiment of the present invention.
Figure 10:
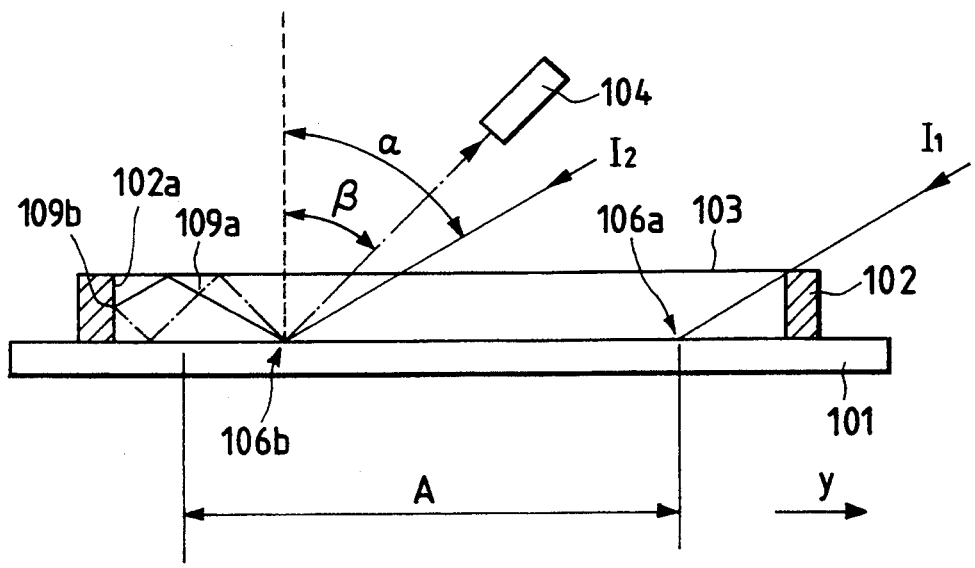
FIG. 10 is a conceptual drawing to illustrate frame stray light in the conventional foreign particle inspection apparatus.

A foreign particle inspection operation is next explained with reference to FIG. 6 and FIG. 7. In FIG. 6, an inspection start position is a position where the incident light I first impinges on the surface to be inspected without being interrupted by the pellicle frame 2, which is a line $S_1$ (corresponding to a line as seen along the direction of a normal line to the reticle at the inspection start point 106a in FIG. 10 as described before). FIG. 6 shows a state of x-directional optical scanning with an incident beam on the line $S_1$. The foreign particle inspection is started from this state, while the reticle to be inspected 1 is carried in the y-direction in FIG. 6. An amount of y-directional movement is controlled by the carrier motion control portion 14 based on the information about the inspection possible area of the photodetectors RL, RR from the judging portion 13, so that an inspection area ($F_1+R_1$) is inspected by the photodetectors RL, RR, and, FR, FL. Since an inspection area $F_1$ cannot be inspected by the photodetectors RR, RL due to influence of stray light, the area $F_1$ is inspected by the photodetectors FL, FR. If the inspection is carried out in the state of FIG. 6 (or if a direction mark M on the reticle 1 resides at the left bottom), the inspection can be carried out between the line $S_1$ and the line $E_1$, but cannot be conducted in an inspection area N.

Figure 7:
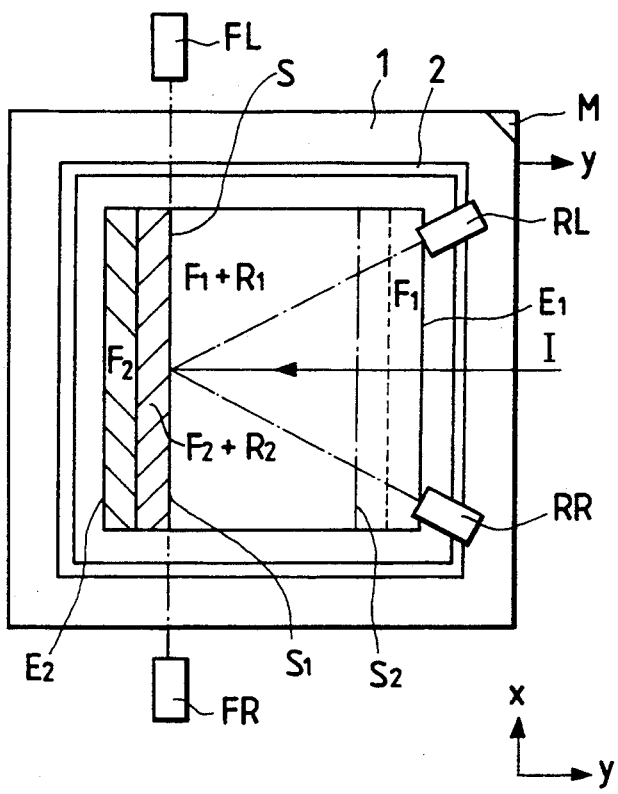
FIG. 7 is a conceptual drawing to illustrate the foreign particle inspection operation in the third embodiment according to the present invention.
Figure 8A:
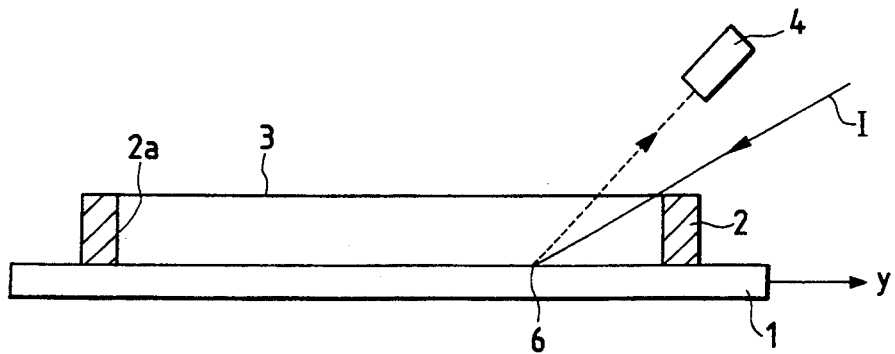
FIGS. 8A to 8C are conceptual drawings to illustrate an operation of the present invention.
Figure 8B:
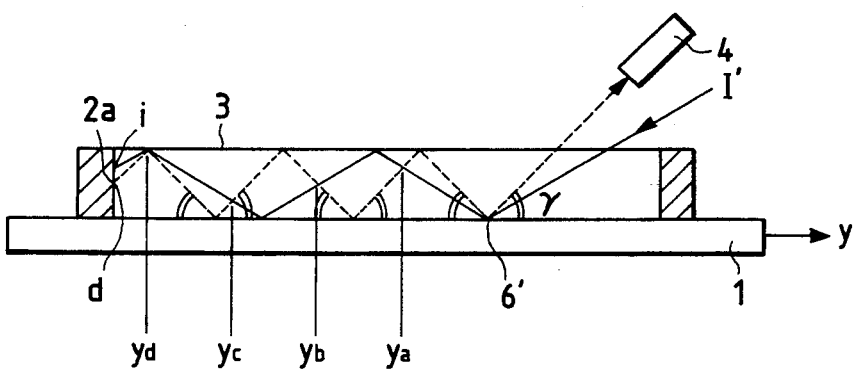
Figure 8C:
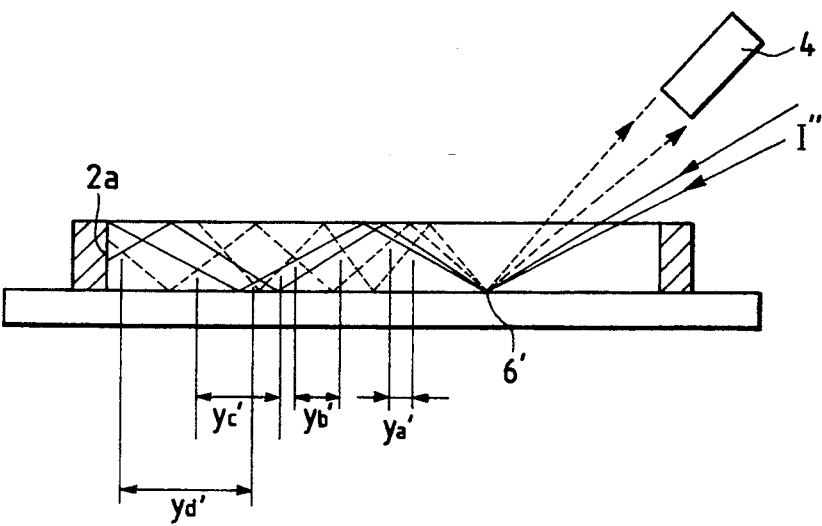
Figure 9:
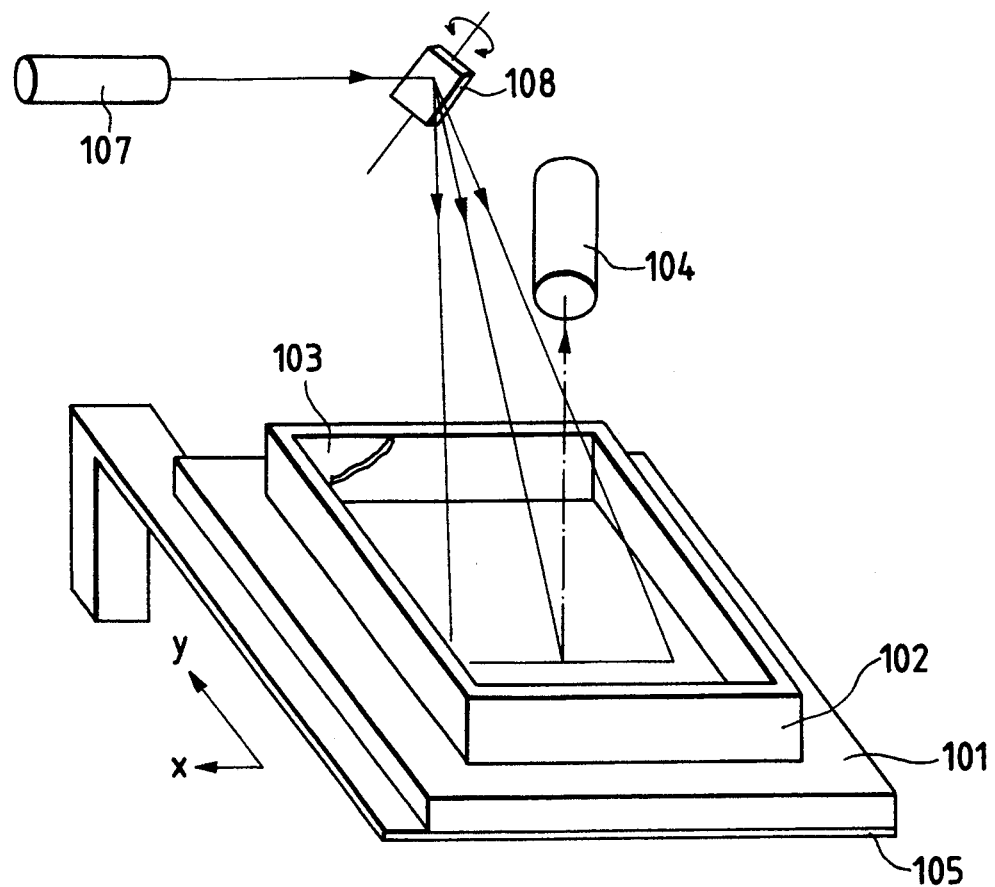
FIG. 9 is a perspective view to show a construction of a conventional foreign particle inspection apparatus.

Then, in order to inspect the inspection area N, the reticle 1 is turned by 180°, whereby the direction mark M on the reticle 1 comes to the right upper position as shown in FIG. 7. A second inspection is carried out in this state. FIG. 7 is a drawing to show a state in which the inspection of the inspection area N is started after the turning of the reticle 1 of FIG. 6. FIG. 7 shows a state of x-directional optical scanning with the incident beam on the line $S_1$. An area ($F_2+R_2$) in FIG. 7 may be inspected by the photodetectors NL, RR, and, FR, FL because it is within the inspection possible area of the photodetectors RL. RR as described, and an inspection area $F_2$ is further inspected by the photodetectors FL, FR. By this, the area N between the line $S_1$ and the line $E_2$, which has not yet been inspected in the first inspection (FIG. 6), is inspected in a second inspection (FIG. 7).

The second inspection may be started from the position $S_2$ where the incident light I first impinges on the surface to be inspected without being interrupted by the pellicle frame 2 similarly as in the first inspection, and inspection results thereof may be integrated in an overlap region of the first and the second inspections, that is, in a region between the line $S_1$ and the line $S_2$.

The entire surface of the necessary inspection range is inspected as described by the four photodetectors FL, FR, and, RR, RL, and an inspection result is displayed on a display portion 17. In the present embodiment, the inspection area of the photodetectors RL, RR is maximized to cover the necessary inspection range without influence of the frame stray light, and therefore the overlap portion of the inspection areas of the photodetectors RL, RR and of the photodetectors FL, FR becomes maximum, whereby the foreign particle inspection may be carried out with more certainty.

Figure 5:
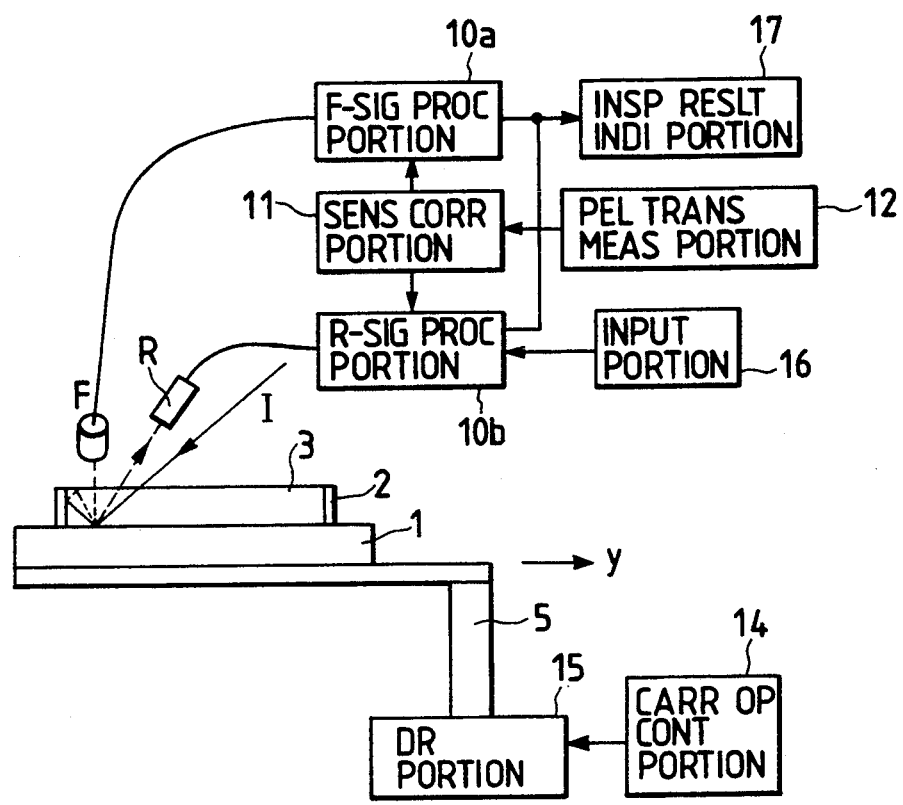
FIG. 5 is a constitutional drawing to show a total construction of the foreign particle inspection apparatus In a fourth embodiment according to the present invention.

FIG. 5 shows a fourth embodiment of the present invention, which is different from the third embodiment in structure to determine the inspection possible area. The arrangement is otherwise the same as that in the third embodiment. Specifically, the fourth embodiment of FIG. 5 has an input portion 16 comprising for example a key board, a bar code reader, or the like in place of the judging portion 13 of FIG. 4, whereby kinds of the pellicle film 3 and the pellicle frame 2 may be input from the outside.

In the present embodiment, inspection possible areas of the respective photodetectors RL, RR, FL, FR are preliminarily measured for each kind of the pellicle film 3 or the pellicle frame 2 mounted on the reticle 1 to be inspected (similarly as in the third embodiment), and measurement results are stored in the apparatus for each kind of the pellicle film 3 or the pellicle frame 2. In actual inspection, an optimum inspection area is set for each of the photodetectors by comparing sorts of the pellicle film 3 and the pellicle frame 2 input into the input portion 16 with data about the above inspection possible areas preliminarily stored. The foreign particle inspection operation after the setting of the inspection area in the same manner as in the third embodiment.

The present embodiment may be further arranged such that sensitivity correction values for the photodetectors FL, FR, RL, RR may be also input from the outside in correspondence to the transmittance of the pellicle film 3, in addition to the data about the inspection possible areas.

Although the above third and fourth embodiments are explained for an example to inspect the reticle surface on which the pellicle film is mounted, it is needless to mention that the foreign particle inspection apparatus of the present invention may be applicable to a foreign particle inspection of the pellicle film itself.

Additionally, the arrangement of the optical system, specifically the arrangement of the plural photodetectors, is not limited to those in the above embodiments. Although the inspection possible areas are measured only for the photodetectors RL, RR in the above embodiments, the inspection area may be determined by measuring an inspection possible area for each of the photodetectors, depending upon the location arrangement of the photodetectors.

Since the foreign particle inspection apparatus of the present invention has a plurality of light receiving means, in which an inspection area is set for each of the light receiving means, a necessary inspection range may be always covered and an overlap portion among the respective inspection areas may be maximized, by combining the plural inspection areas. The inspection precision may be further improved by increasing the overlap portion of the inspection areas of the light receiving means disposed at different positions.

Further, according to the present invention, since there is no extreme restriction on the arrangement of the radiating means and the light receiving means of the inspection light, a preferable arrangement may be set for the radiating means and the light receiving means of the inspection light to improve the detection capability for a foreign particle, which is advantageous in detection of a minute foreign particle or in discrimination of a foreign particle from a minute pattern.

The foreign particle inspection apparatus of the present invention as described is provided with means for determining an inspection area in accordance with an optical property of at least one of the pellicle film and the pellicle frame, so that an inspection area may be efficiently set to cover a maximum area of a necessary inspection range without influence of frame stray light for each kind of at least one of the pellicle film and the pellicle frame to carry out the foreign particle inspection.

What is claimed is:

1. Foreign particle inspection apparatus, comprising:
    radiating means for radiating a light beam toward a surface to be inspected, which is at least one of a surface of a protection film supported by a frame member and a surface of a substrate provided with said protection film;
    light receiving means for receiving light of said beam from said surface to be inspected to output a photoelectric signal;
    detecting means for detecting foreign particles based on the signal of said light receiving means; and
    inspection area setting means for determining in accordance with an optical property of at least one of said frame member and said protection film an inspection area to be irradiated by said light beam on said surface.

2. The apparatus according to claim 1, wherein said inspection area setting means includes measuring means for measuring a value corresponding to a quantity of light scattered by said frame member and received by said light receiving means when said light beam is radiated toward said surface to be inspected, said inspection area setting means determining said inspection area based on a measurement result of said measuring means.

3. The apparatus according to claim 2, wherein said inspection area setting means determines said inspection area based on a value selected among a plurality of pre-stored values measured by said measuring means for at least one of different frame member types and different protection film types.

4. The apparatus according to claim 1, wherein said apparatus comprises input means for inputting information corresponding the optical property of at least one of said frame member and said protection film and wherein said inspection area setting means determines said inspection area based on the information from said input means.

5. Foreign particle inspection apparatus, comprising:
    radiating means for radiating a light beam toward a surface to be inspected, which is at least one of a surface of a protection film supported by a frame member and a surface of a substrate provided with said protection film;
    a plurality of light receiving means for individually receiving light of said beam from said surface to be inspected to output respective photoelectric signals;
    detecting means for detecting foreign particles based on the signals of said light receiving means; and
    inspection area setting means for determining, independently for each of said plurality of light receiving means in accordance with an optical property of at least one of said frame member and said protection film, a respective inspection area to be irradiated by said light beam on said surface.

6. The apparatus according to claim 5, wherein said inspection area setting means includes measuring means for measuring a value corresponding to a respective quantity of light scattered by said frame member and received by each of said plurality of light receiving means when said light beam is radiated toward said surface to be inspected, said inspection area determining each setting said inspection area based on a measurement result of said measuring means.

7. The apparatus according to claim 6, wherein said inspection area setting means determines each inspection area based on a value selected among a plurality of pre-stored values measured by said measuring means for at least one of different frame member types and different protection film types.

8. The apparatus according to claim 5, wherein said apparatus comprises input means for inputting information corresponding to the optical property of at least one of said frame member and said protection film and wherein said inspection area setting means determines each inspection area based on information from said input means.

9. The apparatus according to claim 5, wherein said inspection area setting means maximizes an overlap portion of the respective inspection areas for said plurality of light receiving means.

10. The apparatus according to claim 5, further comprising turning means for turning said substrate by 180° after completion of a first inspection on the surface, wherein, in a second inspection, a result of said first inspection and a result of said second inspection are integrated together in an overlap portion of inspection areas of said first and second inspections.

11. Foreign particle inspection apparatus, comprising:
    a radiating portion for radiating a light beam toward a surface to be inspected, which is at least one of a surface of a protection film supported by a frame member and a surface of a substrate provided with said protection film;
    a light receiving portion for receiving light of said beam from said surface to be inspected to output a photoelectric signal;
    a detecting portion for detecting foreign particles based on the signal of said light receiving means; and
    an inspection area setting portion for determining in accordance with information corresponding to light scattered by said frame member an inspection area to be irradiated by said light beam on said surface.

12. The apparatus according to claim 11, wherein said information includes information corresponding to a reflectivity of said protection film.

13. The apparatus according to claim 11, wherein said radiation portion radiates said light beam obliquely with respect to said surface, and said inspection area setting portion determines said inspection area to exclude a partial area which can be irradiated by said beam and which is adjacent to said inspection area.

14. The apparatus according to claim 13, wherein said inspection area setting portion includes a measuring system for measuring a value corresponding to a quantity of light scattered by said frame member and received by said light receiving portion when said light beam is radiated toward said surface to be inspected, and said inspection area setting portion determines said partial area based on a measurement result of said measuring system.

15. The apparatus according to claim 14, further comprising a drive portion for moving said substrate relative to said light beam and for measuring a position of said substrate, and said inspection area setting portion determines said partial area based on a position of said substrate where said quantity of light does not exceed the threshold value.

16. The apparatus according to claim 11, wherein said inspection area setting portion includes a measuring system for measuring a value corresponding to a quantity of light scattered by said frame member and received by said light receiving portion when said light beam is radiated toward said surface to be inspected, and said inspection area setting portion judges a type of said frame member in accordance with said measured value and selects said inspection area from a plurality of predetermined inspection areas based on the type of said frame member.

17. The apparatus of according to claim 11, further comprising an input portion for inputting information indicating a type of said frame member, wherein said inspection area setting portion selects said inspection area from a plurality of pre-stored inspection areas for different frame member types based on the information inputted into said input portion.

18. Foreign particle inspection apparatus, comprising:
    a radiating portion for radiating a light beam toward a surface to be inspected, which is at least one of a surface of a protection film supported by a frame member and a surface of a substrate provided with said protection film;
    a plurality of light receiving portions for individually receiving light of said beam from said surface to be inspected to output respective photoelectric signals;
    a detecting portion for detecting foreign particles based on the signals of said light receiving portions; and
    an inspection area setting portion for determining, independently for each of said plurality of light receiving portions in accordance with information corresponding to light scattered by said frame member, an inspection area to be irradiated by said light beam on said surface.

19. The apparatus according to claim 18, wherein said information includes information corresponding to a reflectivity of said protection film.

20. The apparatus according to claim 18, wherein said radiating portion radiates said light beam obliquely with respect to said surface, and said plurality of light receiving portions includes first and second light receiving portions for receiving light of said beam coming from said surface along respective axes extending in substantially different directions relative to an incident plane of said light beam, and said inspection area setting portion determines an inspection area excluding a partial area on said surface as an inspection area corresponding to said first light receiving portion and determines an area including said partial area as an inspection area corresponding to said second light receiving portion, said partial area being adjacent to the inspection area corresponding to said first light receiving portion.

21. The apparatus according to claim 20, wherein said inspection area setting portion includes a measuring system for measuring a value corresponding to a quantity of light scattered by said frame member and received by said first light receiving portion when said light beam is radiated toward said surface to be inspected, and determines said partial area based on a measurement result of said measuring system.

22. The apparatus according to claim 21, further comprising a drive portion for moving said substrate relative to said light beam, and a position measuring portion for measuring a position of said substrate, and wherein said inspection area setting portion setting portion determines said partial area based on a position of said substrate where said quantity of light does not exceed a threshold.

23. The apparatus according to claim 20, further comprising an input portion for inputting information indicating a type of said frame member, wherein said inspection area setting portion selects each inspection area from a plurality of pre-stored inspection areas for different frame member types based on the information inputted into said input portion.

24. The apparatus according to claim 20, wherein said inspection area setting portion maximizes an overlap portion of respective inspection areas for said plurality of light receiving portions.

25. The apparatus according to claim 18, wherein said inspection area setting portion includes a measuring system for measuring a value corresponding to a quantity of light scattered by said frame member and received by each said light receiving portion when said light beam is radiated toward said surface to be inspected, and said inspection area setting portion determines each inspection area based on a measurement result of said measuring means.

26. The apparatus according to claim 18, further comprising a turning portion for turning said substrate by 180 degrees after a completion of a first inspection of the surface, wherein, in a second inspection, a result of said first inspection and a result of said second inspection are integrated together in an overlap portion of inspection areas of said first and second inspections.

* * * * *